United States Patent
Magil

(10) Patent No.: US 9,733,263 B2
(45) Date of Patent: Aug. 15, 2017

(54) COLLAGEN IV BINDING ASSAY FOR THE DETECTION OF COLLAGEN VII

(71) Applicant: LOTUS TISSUE REPAIR INC., Cambridge, MA (US)

(72) Inventor: Sheila G. Magil, Arlington, MA (US)

(73) Assignee: LOTUS TISSUE REPAIR INC., Cambridge, MA (US)

( * ) Notice: Subject to any disclaimer, the term of this patent is extended or adjusted under 35 U.S.C. 154(b) by 0 days.

(21) Appl. No.: 14/440,958

(22) PCT Filed: Nov. 7, 2013

(86) PCT No.: PCT/US2013/068971
§ 371 (c)(1),
(2) Date: May 6, 2015

(87) PCT Pub. No.: WO2014/074729
PCT Pub. Date: May 15, 2014

(65) Prior Publication Data
US 2016/0011219 A1  Jan. 14, 2016

Related U.S. Application Data

(60) Provisional application No. 61/723,372, filed on Nov. 7, 2012.

(51) Int. Cl.
*G01N 33/94* (2006.01)
*G01N 33/68* (2006.01)

(52) U.S. Cl.
CPC ......... *G01N 33/94* (2013.01); *G01N 33/6887* (2013.01); *G01N 2333/78* (2013.01)

(58) Field of Classification Search
None
See application file for complete search history.

(56) References Cited

FOREIGN PATENT DOCUMENTS

| EP | 0401370 A1 | 12/1990 |
|---|---|---|
| WO | 2012/149136 | 11/2012 |

OTHER PUBLICATIONS

Extended European Search Report dated Apr. 6, 2016 from European Patent Application No. 13853466.4, pp. 1-9.
Chen, Mei et al. "Interactions of the Amino-terminal Noncollagenous (NC1) Domain of Type VII Collagen with Extracellular Matrix Components. A Potential Role in Epidermal-Dermal Adherence in Human Skin", The Journal of Biological Chemistry, vol. 272, No. 23, Jun. 6, 1997, pp. 14516-14522.
Chen, Mei et al. "Development and Characterization of a Recombinant Truncated Type VII Collagen "Minigene"", The Journal of Biological Chemistry, vol. 275, No. 32, Aug. 11, 2000, pp. 24429-24435.
International Search Report dated Feb. 27, 2014 from International Application No. PCT/US2013/068971, pp. 1-18.
Brittingham, Raymond et al. High-Affinity Binding of the NC1 Domain of Collagen VII to Laminin 5 and Collagen IV, Thomas Jefferson University Jefferson Digital Commons, Aug. 24, 2006, pp. 1-27.
Amano, Satoshi et al. Quantitative analysis of the synthesis and secretion of type VII collagen in cultured human dermal fibroblasts with a sensitive sandwich enzyme-linked immunoassay. Experimental Dermatology, Aug. 29, 2006, vol. 16, pp. 151-155.
Chen, Mei et al. The Carboxyl Terminus of Type VII Collagen Mediates Antiparallel Dimer Formation and Constitutes a New Antigenic Epitope for Epidermolysis Bullosa Acquisita Autoantibodies. The Journal of Biological Chemistry, vol. 276, No. 24, Mar. 27, 2001, pp. 21649-21655.
De Oliveira, Zilda Najjar Prado et al. Immunological mapping in hereditary epidermolysis bullosa. An Bras Dermatol., Jan. 19, 2011, vol. 85, No. 6, pp. 856-861.

*Primary Examiner* — Michael Borin
(74) *Attorney, Agent, or Firm* — MH2 Technology Law Group, LLP

(57) ABSTRACT

The present disclosure features a method of detecting and/or quantifying collagen VII or a fragment thereof in a sample, the method including contacting the sample with collagen IV or a fragment thereof which binds to collagen VII; and contacting the sample with an anti-collagen VII antibody, wherein the anti-collagen VII antibody binds to the NC2 domain of collagen VII; detecting binding of the anti-collagen VII antibody to thereby detect and/or quantify an amount of collagen VII or the fragment thereof in the sample. A method of evaluating or processing a collagen VII preparation is also provided.

17 Claims, 4 Drawing Sheets

Std1 & std2: C7 diluted in blocking buffer

Sample1 &Sample2: C7 diluted in culture medium

COLLAGEN IV BINDING ASSAY FOR THE DETECTION OF COLLAGEN VII

CROSS-REFERENCE TO RELATED APPLICATIONS

This application is a U.S. National Stage application of PCT/US2013/068971 filed Nov. 7, 2013, which claims the benefit of U.S. Provisional Application No. 61/723,372, filed Nov. 7, 2012. The contents of all of which are hereby incorporated by reference in their entirety.

BACKGROUND OF THE INVENTION

Collagen VII is a major component of anchoring fibrils, which help anchor the top layer of the skin, the epidermis, to the underlying dermis, and thus strengthen and stabilize the skin. Collagen VII is encoded by the COL7A1 gene, and mutations in the gene can be associated with epidermolysis bullosa (EB). EB is a group of genetic conditions associated with skin fragility and blistering. Blisters and skin erosions often form in response to minor injury or friction, such as rubbing or scratching. Dystrophic epidermolysis bullosa (DEB) is one of the major forms of epidermolysis bullosa. The signs and symptoms of this condition vary widely among affected individuals. In mild cases, blistering may primarily affect the hands, feet, knees, and elbows; while severe cases can involve widespread blistering that can lead to various complications including vision loss, disfigurement, and other serious medical problems.

COL7A1 mutations associated with DEB impair both collagen VII expression and the ability of collagen VII to form anchoring fibrils. The level of collagen VII expression correlates with the severity of DEB disease with lower collagen VII expression associated with a more severe disease phenotype. Thus methods to accurately detect and/or quantitate the level of collagen VII expression in biological samples would be advantageous for use both in humans as a diagnostic and prognostic index for DEB and in monitoring or evaluating DEB subject response to treatment, as well as in animal and tissue culture models of DEB disease.

SUMMARY OF THE INVENTION

In one aspect, the disclosure features a method of detecting and/or quantifying collagen VII or a fragment thereof in a sample, the method comprising: contacting the sample with collagen IV or a fragment thereof which binds to collagen VII; and detecting binding of collagen VII or a fragment thereof to collagen IV or a fragment thereof which binds to collagen VII, to thereby detect and/or quantifying the amount of collagen VII or fragment thereof in the sample.

In one embodiment, the method detects and/or quantifies full length collagen VII. In one embodiment, the method detects and/or quantifies collagen VII or a fragment thereof comprising both the NC1 and NC2 domains. In certain embodiments, the method detects and/or quantifies a fragment of collagen VII which binds collagen IV.

In certain embodiments, the method further comprises contacting the sample with an anti-collagen VII antibody, which antibody binds collagen VII or a fragment thereof when the collagen VII or fragment thereof is complexed to collagen IV or a fragment thereof, e.g., it binds collagen VII in a collagen VII-collagen IV complex.

In certain embodiments the method comprises: contacting the sample with an anti-collagen VII antibody, which binds to an epitope of collagen VII or a fragment thereof which is accessible after the binding of collagen VII or a fragment thereof to collagen IV or a fragment thereof. In certain embodiments, the anti-collagen VII antibody binds to the NC2 domain of collagen VII. In other embodiments, the anti-collagen VII antibody binds to the NC1 domain of collagen VII.

In certain embodiments the method further comprises contacting the sample with a second antibody, which binds to the anti-collagen VII antibody, e.g., a second antibody that has a detectable label.

In certain embodiments the method further comprises detecting the presence of the anti-collagen VII antibody, e.g., detecting anti-collagen VII antibody bound to collagen VII or a fragment thereof.

In certain embodiments the method further comprises quantifying the amount of anti-collagen VII antibody, e.g., quantifying anti-collagen VII antibody bound to collagen VII or a fragment thereof.

In certain embodiments, the method comprises measuring the level of collagen VII bound to collagen IV.

In certain embodiments, the collagen IV or fragment thereof is disposed on a support, e.g., an insoluble or solid support, e.g., it is support, e.g., an insoluble or solid support, prior to contacting with collagen VII or fragment thereof.

In certain embodiments the sample is biological sample. In certain embodiments the sample is a tissue biopsy, skin biopsy, a biological fluid, blood, or cell lysate, culture medium. In certain embodiments, the sample is a drug product preparation or a drug substance preparation.

In one aspect, the disclosure features a method of detecting and/or quantifying collagen VII or a fragment thereof in a sample, the method comprising:

contacting the sample with collagen VII or a fragment thereof which binds to collagen VII;

contacting the sample with an anti-collagen VII antibody which binds to the NC2 domain of collagen VII;

detecting the binding of the anti-collagen VII antibody;

to thereby detect and/or quantify collagen VII or fragment thereof in the sample.

In one embodiment, the method detects and/or quantifies full length collagen VII. In one embodiment, the method detects and/or quantifies collagen VII or fragment thereof comprising both the NC1 and NC2 domains. In certain embodiments, the method detects and/or quantifies a fragment of collagen VII which binds collagen IV.

In certain embodiments, the method further comprises contacting the sample with an anti-collagen VII antibody, which antibody binds collagen VII or a fragment thereof when the collagen VII or fragment thereof is complexed to collagen IV or a fragment thereof, e.g., it binds collagen VII in a collagen VII-collagen IV complex.

In certain embodiments the method comprises: contacting the sample with an anti-collagen VII antibody, which binds to an epitope of collagen VII or a fragment thereof which is accessible after the binding of collagen VII or a fragment thereof to collagen IV or a fragment thereof.

In certain embodiments the method further comprises contacting the sample with a second antibody, which binds to the anti-collagen VII antibody, e.g., a second antibody that has a detectable label.

In certain embodiments the method further comprises detecting the presence of the anti-collagen VII antibody, e.g., detecting anti-collagen VII antibody bound to collagen VII or a fragment thereof.

In certain embodiments the method further comprises quantifying the amount of anti-collagen VII antibody, e.g., quantifying anti-collagen VII antibody bound to collagen VII or a fragment thereof.

In certain embodiments, the method comprises measuring the level of collagen VII bound to collagen IV.

In certain embodiments, the collagen IV or fragment thereof is disposed on a support, e.g., an insoluble or solid support, e.g., it is support, e.g., an insoluble or solid support, prior to contacting with collagen VII or fragment thereof.

In certain embodiments the sample is biological sample. In certain embodiments the sample is a tissue biopsy, skin biopsy, a biological fluid, blood, or cell lysate, culture medium. In certain embodiments, the sample is a drug product preparation or a drug substance preparation.

Methods disclosed herein are useful, inter alia, for analyzing or processing a collagen VII preparation, e.g., to determine whether to accept or reject a batch of a collagen VII, or to guide or control of a step in the production of collagen VII.

In one aspect, the invention provides a method of evaluating or processing a collagen VII preparation, e.g., a collagen VII drug substance preparation or a collagen VII drug product preparation.

The method includes:

acquiring an evaluation of the presence or amount of collagen VII, e.g., full length collagen VII, in a sample;

providing a determination of whether the value (e.g., a value correlated with absence, presence or amount) determined meets a preselected criteria, e.g., is full length collagen VII present and/or present in a sufficient amount in the sample;

thereby evaluating or processing the collagen VII preparation.

In certain embodiment, the presence or amount of collagen VII is determined by a method described herein.

In certain embodiments, the method includes providing a comparison of the value determined with a reference value to thereby evaluate the sample. In certain embodiments, the comparison includes determining if the test value has a preselected relationship with the reference value, e.g., determining if it meets the reference value. The value need not be a numerical value but can be merely an indication of whether the subject entity (e.g., full length collagen VII) is present.

In certain embodiments, the method includes determining if a test value is equal to or greater than a reference value, if it is less than or equal to a reference value, or if it falls within a range (either inclusive or exclusive of one or both endpoints).

In certain embodiments, the test value, or an indication of whether the preselected relationship is met, can be memorialized, e.g., in a computer readable record.

In certain embodiments, the sample is further processed depending on whether a preselected relationship is met, e.g., a decision or step is taken, e.g., the sample is classified, selected, accepted or discarded, released or withheld, processed into a drug product, shipped, moved to a different location, formulated, labeled, packaged, released into commerce, or sold or offered for sale, depending on whether the preselected relationship is met. E.g., based on the result of the determination, or upon comparison to a reference standard, the batch from which the sample is taken can be processed, e.g., as described above. In certain embodiments, the preselected relationship is met, and the sample is processed into drug product or formulated. In certain embodiments, the preselected relationship is met, and the sample is subjected to purification.

In certain embodiments, the methods described herein are useful from a process standpoint, e.g., to monitor or ensure batch-to-batch consistency or quality, or to evaluate a sample with regard to a reference, e.g., a preselected value. In certain embodiments, methods described herein can be used to determine if a test batch of a collagen VII can be expected to have one or more of the properties of the collagen VII. In certain embodiments, the methods described herein can be used to determine the stability and/or shelf life of a collagen VII drug product preparation.

DETAILED DESCRIPTION OF THE INVENTION

Figure 1:
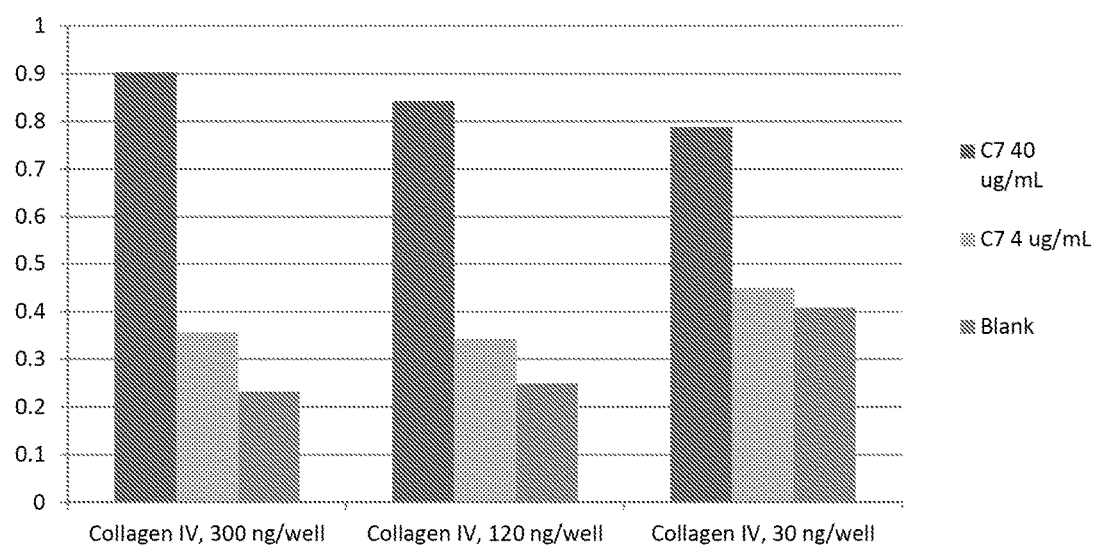
FIG. 1 shows the level of collagen VII detected using the following experimental conditions: a concentration of 300 ng/well collagen IV, 120 ng/well of collagen IV, or 30 ng/well of collagen IV using 10 mM acetic acid coating buffer; a dilution of 1:300 of anti-collagen VII antibody (anti-NC1 domain Ab (Sigma, LH7.2); and a wash buffer of 1% BSA in PBS containing 0.05% Tween® 20.

The invention provides methods for detecting and/or quantifying collagen VII.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sample" as the term is used herein, refers to obtaining possession of a sample, e.g., a tissue sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

The term "antigen" is used herein in its broadest sense, and refers to any molecule, cell, virus, or particle. For example, an antigen can include but is not limited to a protein molecule, a peptide molecule, an RNA molecule, a DNA molecule, a chemical molecule, a traditional antibody (e.g., two heavy chains and two light chains), a recombinant antibody, a fragment of a recombinant antibody, a fragment of a traditional antibody, a bacterial cell, a virus particle, a eukaryotic cell, a particle, and a product comprising cross-linking any two or more of the above. An antigen can be in a pure form, or it can exist in a mixture. An antigen can be in a modified form (e.g., modified by chemicals) or an unmodified form.

The term "antibody" is used herein in its broadest sense, and refers to a polypeptide that binds to "an antigen". An antibody can include, but is not limited to, a traditional antibody, a fragment of a traditional antibody, a fragment of a traditional antibody containing an antigen binding site, a recombinant antibody, a recombinant antibody containing an antigen binding site, a protein which binds to an antigen, a bispecific antibody, a multi-specific antibody, a bivalent antibody, a multivalent antibody, a polyclonal antibody, a monoclonal antibody, an agonist antibody, an antagonist antibody, a neutralizing antibody, and a product comprising cross-linking any two or more of the above. An antibody can be in pure form, or it can exist in a mixture. An antibody can be in a modified form (e.g., modified by a chemical) or an unmodified form.

The term "detecting" is used herein in its broadest sense to include both qualitative and quantitative measurements of a target molecule. A detecting method as described herein can used to identify the mere presence of collagen VII in a sample. The method can also be used to test whether collagen VII in a sample is at a detectable level. The method can be used to quantify the amount of collagen VII in a sample and further to compare the collagen VII levels from different samples.

The term "room temperature" as used herein, refers to around or about 25° C.

General Description of the Process

The methods described herein may be characterized as an enzyme linked immunosorbant assay (ELISA). The general method of an ELISA and ELISA variations are known to those skilled in the art. The following is a general description of the methods described herein solely to illustrate the timeline of steps involved in the methods. The disclosure should not be limited to or restricted to this description in anyway. The components are merely described for purposes of illustration.

A coating agent (e.g., collagen IV) is immobilized onto a solid support (e.g., microtiter plate). Once the coating agent has been immobilized on the solid support the remaining binding sites on the solid support are blocked using a blocking buffer (e.g., 1% BSA in 1×PBS). The blocking buffer contains a component capable of non-specifically binding to the solid support to saturate the open binding sites, therefore preventing binding of free ligand to any excess sites on the solid support. The specific conditions of the coating and blocking incubation periods are selected to maximize coating of the solid support; and variations are known to those skilled in the art. After coating and blocking of the solid support, the standards (e.g., recombinant collagen VII) and/or samples (e.g., biological samples being tested for collagen VII) to be analyzed are appropriately diluted in a suitable dilution buffer (e.g. 1% BSA in 1×PBS) and added to the immobilized support. The specific conditions of the standard/sample incubation period are selected to maximize sensitivity of the assay and minimize dissociation; variations are known to those skilled in the art.

Any non-immobilized standard/sample (e.g., collagen VII) is removed by washing the solid support with a suitable wash buffer (e.g., 1.0% BSA in 1×PBS+0.05% Tween® 20), a suitable number of times. The specific wash buffer and number washes at any wash step are selected to minimize background and maximize sensitivity; and variations are known to those skilled in the art. Any immobilized standard/sample (e.g., collagen VII) can then be detected either indirectly or directly. For indirect detection, an antibody (primary antibody) against the antigen of interest in the standard/sample (e.g., anti-collagen VII antibody) is added to the solid support; and the incubation conditions selected to maximize signal amplification. Any non-immobilized antibody is then removed by washing the solid support with a suitable washing buffer, a suitable number of times. An antibody conjugated to a moiety that is detectable by some means (detecting antibody) and capable of binding to the primary antibody is then added to the solid support. Any unbound detecting antibody is then removed by washing the solid support with a suitable washing buffer, a suitable number of times. The level of the antigen of interest in the standard/sample (e.g., collagen VII) bound to the coating agent can be determined using a detection system compatible with the detection antibody employed. A suitable detection means will be known to one of skill in the art.

In the instance direct detection of the antigen of interest in the standard/sample (e.g., collagen VII) is employed, the primary antibody is conjugated to a moiety that is detectable by some means and is thus also the detecting antibody, i.e., the primary antibody and detecting antibody are the same. Any unbound detecting antibody is then removed by washing the solid support with a suitable washing buffer, a suitable number of times. The level of the antigen of interest in the standard/sample (e.g., collagen VII) bound to the coating agent can be determined using a detection system compatible with the primary/detection antibody employed. A suitable detection system will be known to one of skill in the art.

Collagen IV

The methods described herein can provide collagen IV, or a collagen VII binding fragment of collagen IV, as a coating agent to be immobilized onto a solid support. Recombinant collagen IV can be purchased or made by standard molecular biology techniques known to those skilled in the art.

Anti-Collagen VII Antibodies

The methods described herein can provide an anti-collagen VII antibody for the detection of collagen VII bound to an agent on an immobilized substrate, e.g., collagen IV. Anti-collagen VII antibodies can be purchased or made by standard molecular biology techniques. An anti-collagen VII antibody can bind to a region of the NC2 domain of collagen VII. An anti-collagen VII antibody can bind to a region of the NC1 domain of collagen VII. An anti-collagen VII antibody can be capable of binding only to full length collagen VII. An anti-collagen VII antibody can be capable of binding to the full length collagen VII and truncated forms of collagen VII. The antibodies can be derived from any species. The antibodies can be monoclonal or polyclonal or any variation of an "antibody" described herein. The antibodies can be directly detectable through the attachment of a detectable label, e.g., a chemical modification, enzyme conjugation, fluorescent dye labeling, luminescence labeling, etc. The antibodies can also not be directly detectable, and require a secondary means for detection. Antibodies with these various properties can be purchased or made by standard molecular biology techniques. The anti-collagen VII antibody can include but is not limited to, e.g., pAb anti-NC2 domain Collagen VII (Santa Cruz, H120). The anti-collagen VII antibody can include but is not limited to, e.g., pAb anti-NC2 domain Collagen VII (Santa Cruz, H120); mAb anti-Collagen VII (Abcam, [LH7.2]); mAb anti-Collagen VII (Abcam, [2Q636]); mAb anti-Collagen VII (Millipore, [clone 185, MAB2501]); pAb anti-NC1 domain Collagen VII (Calbiochem); mAb anti-NC1 domain Collagen VII (R&D Systems, [NP185]); or mAb anti-triple helical region Collagen VII (Santa Cruz, [4D2]). Additional antibodes include anti-NC2 domain Collagen VII antibodies disclosed in (Bruckner-Tuderman et al. (1995) *The Journal of Cell Biology* 131: 551-559.

Samples

Samples can include but are not limited to, biological samples from any animal, including but not limited to mammals, e.g., dogs, mice, and humans. Biological samples can include but are not limited to biopsies, e.g., tissue biopsy, e.g., skin biopsy; biological fluids, e.g., blood, saliva, cord fluid, plasma, urine, amniotic fluid, serum, vitreous fluid, lymph fluid, synovial fluid, follicular fluid, milk, cerebro-spinal fluid, sputum tears, perspiration, mucus, cell lysate and culture medium. A biological sample may refer to a homogenate, lysate, or extract prepared from a whole organism or a subset of its tissues, cells or component parts, or a fraction or portion thereof. A biological sample may refer to a homogenate, lysate, or extract prepared from a biopsy, e.g., tissue biopsy, e.g., a skin biopsy.

In some embodiments, the sample is a drug substance preparation or drug product preparation. The term "drug product preparation" refers to a collagen VII preparation having the purity required for and being formulated for pharmaceutical use. The term "drug substance preparation" refers to a collagen VII preparation for pharmaceutical use but is not necessarily in its final formulation and/or comprises one or more non-product contaminant.

A sample may be modified prior to use, such as by dilution, purification, purification of various fractions, centrifugation and the like.

Solid Support

Solid supports can include any surface to which a coating agent, e.g., collagen IV, or equivalent thereof can be immobilized on. Solid supports used for immobilization can be any inert support or carrier that is essentially water insoluble and useful in immunometric assays, including supports in the form of, e.g., surfaces, particles, porous matrices, etc. Examples of commonly used supports include small sheets, Sephadex, polyvinyl chloride, plastic beads, and assays plates or test tubes manufactured from polyethylene, polypropylene, polystyrene, and the like including 96-wel microtiter plates, as well as particulate materials such as filter paper, agarose, cross-linked dextran, and other polysaccharides. Alternatively, reactive water insoluble matrices such as cyanogens bromide-activated carbohydrates are suitably employed for coating reagent immobilization. The immobilized coating agent can be coated on a microtiter plate, for instance a multi-well microtiter plate that can be used to analyze several samples at one time. Solid support surfaces can also include but are not limited to, a membrane, e.g., a nitrocellulose membrane, a polytetrafluorethylene membrane, cellulose acetate membrane, cellulose nitrate membrane, a solid surface coated with molecules containing hydrophobic groups, a solid surface coated with molecules containing hydrophilic groups. Solid support surfaces can be in the form of a microtiter plate, e.g., a polystyrene microtiter plate, cell culture plate, or any variation thereof.

Primary Antibody

The term "primary antibody" refers to an antibody which binds directly to the antigen of interest (e.g., collagen VII). The primary antibody can also be a detecting antibody. The antibody can be derived from any species, including but not limited to, human, rabbit, mouse, rat, sheep, goat, chicken, human, horse, dog, cat, hamster, monkey, chimpanzee, ovine, equine, porcine, bovine, primate, etc.

Detecting Antibody

The term "detecting antibody" or "detection antibody" refers to a labeled antibody used to detect an "antigen" or "antibody". The detecting antibody can also be a primary antibody. The antibody can be derived from any species, including but not limited to, human, rabbit, mouse, rat, sheep, goat, chicken, human, horse, dog, cat, hamster, monkey, chimpanzee, ovine, equine, porcine, bovine, primate, etc. The label used on the detecting antibody can be any detectable functionality that does not interfere with the binding of collagen VII to the antibody. Examples of suitable labels are those numerous labels known for use immunoassays, including moieties that may be detected directly, such as fluorochrome, chemiluminscent, and radioactive labels, as well as moieties, such as enzymes, that must be reacted or derivatized to be detected. Suitable labeling methods that can be used in the present invention include, but are not limited to, isotope labeling, chemical modification, enzyme conjugation, fluorescent dye labeling, luminescence labeling, and other labeling methods commonly known to those skilled in the art.

Those skilled in the art will be aware of a variety of labeling methods for an antibody or other detection agent. Labeling methods include but are not limited to, an enzyme such as horse radish peroxide (HRP), alkaline phosphatase (AP), beta-galactosidase, glucoamylase, lysozyme, saccharide oxidases, e.g., glucose oxidase, glactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, biotin/streptavidin, biotin/Streptavidin-fl-galactosidase with MUG, spin labels, bacteriophage labels, stable free radicals, or other enzymes and the like. A detection agent can also be labeled with radioactive isotopes, e.g., $^{125}$I, $^{32}$P, $^{14}$C, $^{3}$H, and $^{131}$I, or other isotope. Fluorescent labels can include but are not limited to fluorophores such as rare earth cheats or fluorescein and its derivatives, rhodamine and its derivatives, dansyl, umbelliferone, luceriferases, e.g., firefly luciferase and bacterial luciferase (U.S. Pat. No. 4,737,456), luciferin, fluorescin isothiocynate (FITC), rhodamine, Texas Red, Alexa488, Cy5, Cy3, Alexa610, 7-AAD, propidium iodide, Cy7, phycoerythrin, etc. A detection agent can be labeled by a fluorochrome (a fluorescent dye) that can be detected by fluorescent plate reader, a fluorescent microscope, a fluorometer, a camera, or scanner. A detection agent can also be labeled by a lumichrome which can be detected by luminescence methods. Alternatively a detection agent can be labeled biotin, which can bind to avidin or streptavidin. Avidin or streptavidin can be used as detection agents which can bind to biotin, biotinylated antibodies, or biotinylated polypeptides.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al. Nature 144:945 (1962); David et al. Biochemistry 13:1014-1021 (1974); Pain et al. J. Immunol. Methods 40:219-230 (1981); and Nygren J. Histochem. and Cytochem. 30:407-412 (1982). Preferred labels herein are fluorescent to increase amplification and sensitivity to 8 pg/ml, more preferably biotin with streptavidin-β-galactosidase and MUG for amplifying the signal.

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. Langone and H. Van Vunakis, Vol. 73 (Academic Press, New York, N.Y., 1981), pp. 147-166.

Detection System

The term "detection system" refers to a means which can be used to give a readout comprising information related to the presence, quantity or relative amount of a protein or agent in a sample. The choice of a detection system depends on the choice of the detection antibody used. For example, if a detecting antibody is labeled with an enzyme, in which a chemical reaction can result in color or a chemiluminescence signal; the detection system may include a suitable substrate and any necessary reagents associated with the chemical reaction and a means of detecting the chemical reaction, for example, visual inspection, a device capable of detecting the signal, e.g., an absorbance plate reader, a chemiluminescence plate reader, CCD camera, etc; alternatively, if the detection antibody is fluorescently labeled, a fluorescence microscope, a fluorescence plate reader, a fluorescence cell sorter, a fluorescence scanner, camera, etc. may be used; alternatively, if the detecting antibody is isotope labeled, X ray film or other isotope sensitive material may be used.

Those skilled in the art will be aware of different detection systems suitable for use. These detection systems can include, for example, detection systems using chromogenic reactions of reporter enzymes such as horse radish peroxidase (HRP) or alkaline phosphatase (AP) or the like. The reporter enzymes can use different substrates for chromogenic detection, for example, HRP can use 4 CN (4-chloro-1-napthol), DAB/NiCl$_2$ (3,3'-diaminobenzidine/NiCl$_2$) or TMB as substrates for chromogenic detection. Fluorescent labels include but are not limited to fluorescin isothiocynate (FITC), rhodamine, Texas Red, Alexa488, Cy5, Cy3, Alexa610, 7-AAD, propidium iodide, Cy7, phycoerythrin, etc. Various and appropriate stopping agents can be used to end a detection reaction. The specific stopping agent used will depend on the detection agent used and will be known to one of skill in the art. For example, 1M sulfuric acid can be used as a stopping substrate for detection systems using the horse radish peroxidase enzyme.

Blocking, Wash, and Dilution Buffers

Blocking buffers can be used to block any remaining binding sites on the solid support post incubation with the coating agent. Examples of blocking buffers include but are not limited to, BSA, e.g., BSA in 1×PBS, e.g., 1% BSA in 1×PBS, 1-10% BSA in 1×PBS, 1-20% BSA in 1×PBS, 1-50% BSA in 1×PBS; non-fat milk, casein, fish gelatin, or other chemical reagent. Any of the reagents described above or other suitable chemical reagent can be diluted in any suitable buffer, e.g., phosphate buffered saline (PBS) or tris buffered saline (TBS).

Wash buffers may be used to remove unbound components at various steps. Examples of wash buffers include but are not limited to, BSA, e.g., BSA in 1×PBS, e.g., 1% BSA in 1×PBS, 1-10% BSA in 1×PBS, 1-20% BSA in 1×PBS, 1-50% BSA in 1×PBS; BSA in 1×PBS containing Tween® 20, e.g., BSA in 1×PBS containing 0.05% Tween® 20, 1% BSA in 1×PBS containing 0.05% Tween® 20, 1% BSA in 1×PBS containing 0.05-1% Tween® 20; Tween® 20, e.g., Tween® 20 in 1×PBS, e.g., 0.05% Tween® 20 in 1×PBS; non-fat milk, casein, fish gelatin, or other chemical reagent. Washing buffers can include any of the following BSA, non-fat milk, casein, fish gelatin, or other chemical agent in solution with Triton X 100 or Tween® 20 or the like. These solutions can be diluted in any suitable buffer, including but not limited to phosphate buffered saline (PBS), tris-buffered saline (TBS).

Wash steps can be carried out multiple times, and will depend on the wash buffer employed. For example, washing steps can be repeated once, twice, three, four, five, six, seven, eight, nine, ten, or more than ten times at a given wash period. One of skill in the art will be able to determine the number of wash steps necessary based on the wash buffer used and other experimental conditions.

Buffers used to dilute any standards, samples, antibodies, or detection agents will be known to those skilled in the art and can include but are not limited to BSA, e.g., BSA in 1×PBS, e.g., 1% BSA in 1×PBS, 1-10% BSA in 1×PBS, 1-20% BSA in 1×PBS, 1-50% BSA in 1×PBS; non-fat milk, casein, fish gelatin, or other chemical reagent. In some instances the buffer used to dilute any standards, samples, antibodies, or detection agents will be the same agent used as a blocking buffer.

Incubation Time Periods and Temperatures

Appropriate incubation periods for various steps can be determined by one of skill in the art. The time period for a specific incubation step may be altered due to a change in the temperature of the incubation step, and likewise a change in the time of an incubation step may necessitate a change in the temperature of the incubation step. The coating step may be carried out for example, overnight at or about 4° C., overnight at or about 2-10° C., 4 hours at or about 37° C., 2-4 hours at or about 37° C., 1-4 hours at or about 37° C., 4 hours at or about 32° C., 2-4 hours at or about 32° C., 1-4 hours at or about 32° C. The blocking step may be carried out for example, for 1 hour at or about 32° C.; 1-2 hours at or about 32° C.; overnight at or about 4° C. The standard/sample incubation step can be carried out for example, for 2 hours at or about 32° C.; 1-2 hours at or about 32° C.; overnight at or about 4° C. The primary antibody or primary/detecting antibody incubation step may be carried out for example, for 1 hour at or about 32° C.; 1-2 hours at or about 32° C.; overnight at or about 4° C. The incubation period and temperature of any detecting system will be dependent on the exact detecting antibody employed, and will be known to those skilled in the art.

Kits

Kits comprising one or more components useful for performing the methods described herein can include but are not limited to, any necessary components, reagents, or materials necessary to perform methods described herein, and/or instructions for performing the methods described herein. The kit can optionally include any additional washing agents, incubation containers, solid support surfaces, and the like for carrying out the methods described herein.

The kit may comprise kit a solid support for the coating agents, which may be provided as a separate element or on which the coating agents are already immobilized. Hence, the coating agent in the kit may be immobilized on a solid support, or they may be immobilized on such support that is included with the kit or provided separately from the kit. The coating agents may be coated on a microtiter plate. The primary antibody may be unlabeled or labeled. The primary antibody may be labeled and also be in the detecting antibody. Where the label is an enzyme, the kit may include substrates and cofactors required by the enzyme, and where the label is a fluorophore, the kit may include a dye precursor that provides the detectable chromophore. The kit may also contain instructions for carrying out the assay, and/or a reference standard (e.g., purified collagen VII, e.g., recombinantly produced collagen VII), as well as other additives such as stabilizers, washing and incubation buffers, and the like.

The methods described herein are also described in the following non-limiting examples, which are intended to be illustrative only, as numerous modifications and variations therein, will be apparent to those skilled in the art. Those skilled in the art will be aware of modifications to further improve the signal to noise ratio. These modifications include but are not limited to, adding or modifying one or multiple steps.

EXEMPLIFICATION

Example 1. Development of Collagen IV Binding Assay for the Quantification of Collagen VII Numerous experimental conditions were tested in developing the methods described herein. Exemplary conditions presently described are not intended to be limiting. Experimental conditions subject to testing included, the concentration of collagen IV used as coating agent; the composition of the coating buffer; the concentration of the anti-collagen VII antibody; the composition of the wash buffer; the composition of the standard/sample dilution buffer; the temperature of various incubation periods, the time of various incubation periods, and the number of washes employed at various wash steps.

As described above in the General Description of the Process the methods described herein can in general be conducted as an ELISA. Exemplary results of various experimental conditions are outlined below.

Data presented in Table 1 and Table 2 was acquired using the following experimental conditions: a 10 mM acetic acid coating buffer; a wash buffer of 1% BSA in 1×PBS containing 0.05% Tween® 20; and a dilution of 1:300 of anti-collagen VII antibody, either the mAb anti-NC1 domain Collagen VII antibody or the pAb anti-NC2 domain Collagen VII. Table 1 shows the amount of collagen VII detected (OD) using a concentration of 3 µg/well collagen IV; and Table 2 shows the amount of collagen VII detected (OD) using a concentration of 0.3 µg/well collagen IV.

TABLE 1

Detection of collagen VII by collagen IV binding assay utilizing 3 µg/well collagen IV in 10 mM acetic acid coating buffer.

| Collagen VII [µg/mL] | mAb anti-NC1 domain Collagen VII (Sigma LH7.2) [OD] | | | pAb anti-NC2 domain Collagen VII (Santa Cruz, H120) [OD] | | |
|---|---|---|---|---|---|---|
| 40 | 2.4424 | 2.2701 | 2.2274 | 1.284 | 1.1335 | 1.1599 |
| 0 | 1.0568 | 1.0005 | 0.9397 | 0.9516 | 1.0522 | 0.8088 |

TABLE 2

Detection of collagen VII by collagen IV binding assay utilizing 0.3 µg/well collagen IV in 10 mM acetic acid coating buffer.

| Collagen VII [µg/mL] | mAb anti-NC1 domain Collagen VII (Sigma LH7.2) [OD] | | | pAb anti-NC2 domain Collagen VII (Santa Cruz, H120) [OD] | | |
|---|---|---|---|---|---|---|
| 40 | 2.4085 | 2.3356 | 2.2056 | 1.258 | 1.2379 | 1.1889 |
| 0 | 1.12 | 1.1136 | 1.037 | 0.9528 | 0.8994 | 0.9539 |

Data presented in Table 3 and Table 4 was acquired using the following experimental conditions: a 20 mM $Na_2CO_3$ pH 9.2 coating buffer; a wash buffer of 1% BSA in 1×PBS containing 0.05% Tween® 20; and a dilution of 1:300 of anti-collagen VII antibody, either the mAb anti-NC1 domain Collagen VII antibody or the pAb anti-NC2 domain Collagen VII. Table 3 shows the amount of collagen VII detected (OD) using a concentration of 3 µg/well collagen IV; and Table 4 shows the amount of collagen VII detected (OD) using a concentration of 0.3 µg/well collagen IV.

TABLE 3

Detection of collagen VII by collagen IV binding assay utilizing 3 µg/well collagen IV in 20 mM $Na_2CO_3$ pH 9.2 coating buffer.

| Collagen VII [µg/mL] | mAb anti-NC1 domain Collagen VII (Sigma LH7.2) [OD] | | pAb anti-NC2 domain Collagen VII (Santa Cruz, H120) [OD] | |
|---|---|---|---|---|
| 40 | 1.6204 | 1.4709 | 0.6438 | 0.5074 |
| 0 | 0.6291 | 0.5117 | 0.5441 | 0.4815 |

TABLE 4

Detection of collagen VII by collagen IV binding assay utilizing 0.3 µg/well collagen IV in 20 mM $Na_2CO_3$ pH 9.2 coating buffer.

| Collagen VII [µg/mL] | mAb anti-NC1 domain Collagen VII (Sigma LH7.2) [OD] | | pAb anti-NC2 domain Collagen VII (Santa Cruz, H120) [OD] | |
|---|---|---|---|---|
| 40 | 1.941 | 1.922 | 0.5562 | 0.5573 |
| 0 | 0.5502 | 0.4787 | 0.4784 | 0.6 |

Data presented in Table 5 and FIG. 1 was acquired using 10 mM acetic acid coating buffer; a dilution of 1:300 of anti-collagen VII antibody (anti-NC1 domain Ab (Sigma, LH7.2); and a wash buffer of 1% BSA in PBS containing 0.05% Tween® 20. Table 5 and FIG. 1 show the amount of collagen VII detected (OD) using a concentration of 300 ng/well collagen IV, 120 ng/well of collagen IV, and 30 ng/well of collagen IV.

TABLE 5

Detection of collagen VII by collagen IV binding assay utilizing 300 ng/well; 120 ng/well; and 30 ng/well of collagen IV in 10 mM acetic acid coating buffer.

| Collagen VII [ug/mL] | Collagen IV, 300 ng/well [OD] | | | Collagen IV, 120 ng/well [OD] | | | Collagen IV, 30 ng/well [OD] | | |
|---|---|---|---|---|---|---|---|---|---|
| 40 | 0.8991 | 0.9597 | 0.8498 | 0.8162 | 0.8712 | 0.8394 | 0.787 | 0.7715 | 0.8133 | 0.7804 |
| 4 | 0.3627 | 0.3741 | 0.3316 | 0.3297 | 0.3448 | 0.3558 | 0.3746 | 0.4352 | 0.4764 | 0.5154 |
| 0 | 0.2472 | 0.2277 | 0.2214 | 0.2096 | 0.2639 | 0.2746 | 0.3274 | 0.4069 | 0.4234 | 0.4746 |

Figure 2:
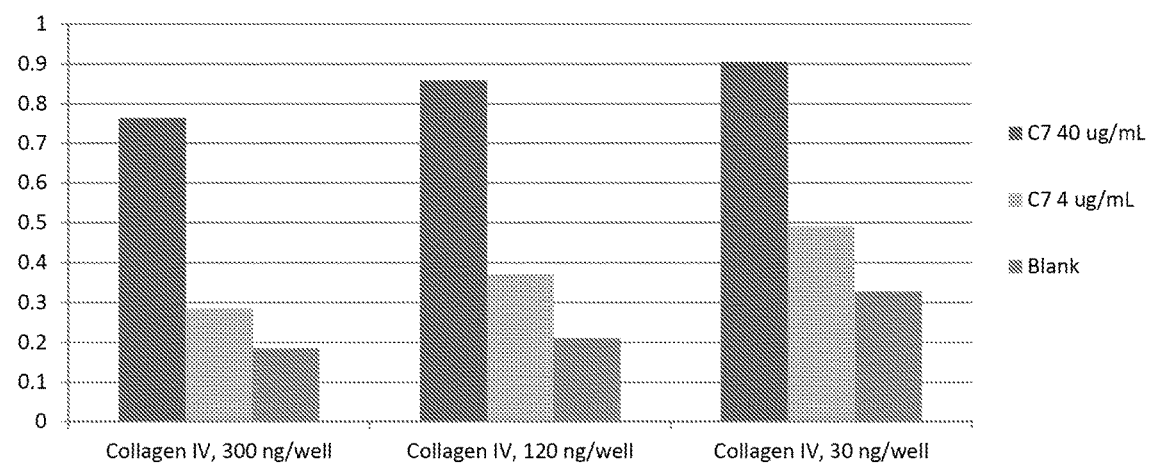
FIG. 2 shows the level of collagen VII detected using the following experimental conditions: a concentration of 300 ng/well collagen IV, 120 ng/well of collagen IV, or 30 ng/well of collagen IV, using 20 mM $Na_2CO_3$ pH 9.2 coating buffer; a dilution of 1:300 of anti-collagen VII antibody (anti-NC1 domain Ab (Sigma, LH7.2); and a wash buffer of 1% BSA in PBS containing 0.05% Tween® 20.

Data presented in Table 6 and FIG. 2 was acquired using 20 mM $Na_2CO_3$ pH 9.2 coating buffer; a dilution of 1:300 of anti-collagen VII antibody (anti-NC1 domain Ab (Sigma, LH7.2); and a wash buffer of 1% BSA in PBS containing 0.05% Tween® 20. Table 6 and FIG. 2 show the amount of collagen VII detected (OD) using a concentration of 300 ng/well collagen IV, 120 ng/well of collagen IV, and 30 ng/well of collagen IV.

TABLE 6

Detection of collagen VII by collagen IV binding assay utilizing 300 ng/well; 120 ng/well; and 30 ng/well of collagen IV in 20 mM $Na_2CO_3$ pH 9.2 coating buffer.

| Collagen VII [ug/mL] | Collagen IV, 300 ng/well [OD] | | | Collagen IV, 120 ng/well [OD] | | | Collagen IV, 30 ng/well [OD] | | |
|---|---|---|---|---|---|---|---|---|---|
| 40 | 0.7624 | 0.7646 | 0.7605 | 0.8783 | 0.8371 | 0.8594 | 0.9151 | 0.9402 | 0.8751 | 0.8878 |
| 4 | 0.2877 | 0.2812 | 0.2851 | 0.3239 | 0.3802 | 0.4133 | 0.4661 | 0.4444 | 0.5043 | 0.5474 |
| 0 | 0.1902 | 0.1792 | 0.1851 | 0.1969 | 0.2048 | 0.2313 | 0.2875 | 0.3238 | 0.314 | 0.3865 |

Data presented in Table 7 was acquired using the following experimental conditions: 120 ng/well collagen IV in 20 mM $Na_2CO_3$ pH 9.2 coating buffer; a wash buffer of 0.05% Tween® 20 in 1×PBS. Table 7 shows the amount of collagen VII detected (OD) using a dilution of 1:300; 1:1000; and 1:3000 of anti-collagen VII antibody (anti-NC1 domain Ab (Sigma, LH7.2).

TABLE 7

Detection of collagen VII by collagen IV binding assay utilizing a dilution of 1:300; 1:1000; and 1:3000 of anti-collagen VII antibody (anti-NC1 domain Ab (Sigma, LH7.2) with a wash buffer of 0.05% Tween® 20 in 1XPBS.

| C7 ug/mL | 1:300 dilution of anti-NC1 [OD] | | | 1:1000 dilution of anti-NC1 [OD] | | | 1:3000 dilution of anti-NC1 [OD] | | |
|---|---|---|---|---|---|---|---|---|---|
| 100 | 0.82 | 0.8806 | 0.8361 | 0.7955 | 0.7867 | 0.6834 | 0.6585 | 0.6554 | 0.6116 |
| 50 | 0.8954 | 0.8003 | 0.8082 | 0.7424 | 0.7745 | 0.7414 | 0.5712 | 0.657 | 0.6088 |
| 25 | 0.6397 | 0.6447 | 0.6523 | 0.5335 | 0.5888 | 0.5501 | 0.5173 | 0.5142 | 0.5256 |
| 12.5 | 0.4984 | 0.4872 | 0.5263 | 0.4301 | 0.4018 | 0.3853 | 0.3658 | 0.3493 | 0.3497 |
| 6.3 | 0.3773 | 0.4144 | 0.3808 | 0.3292 | 0.3301 | 0.3129 | 0.3178 | 0.3077 | 0.292 |
| 3.1 | 0.298 | 0.2968 | 0.3109 | 0.2818 | 0.2495 | 0.2374 | 0.2448 | 0.2173 | 0.2112 |
| 1.6 | 0.2856 | 0.2721 | 0.2917 | 0.2463 | 0.2228 | 0.2167 | 0.208 | 0.1973 | 0.1864 |
| 0 | 0.2205 | 0.2121 | 0.2172 | 0.1693 | 0.1744 | 0.1506 | 0.1453 | 0.1469 | 0.1349 |

Data presented in Table 8 was acquired using 120 ng/well collagen IV in 20 mM $Na_2CO_3$ pH 9.2 (coating buffer); and a wash buffer of 1% BSA in PBS containing 0.05% Tween® 20. Table 8 shows the amount of collagen VII detected (OD) using a dilution of 1:300; 1:1000; and 1:3000 of anti-collagen VII antibody (anti-NC1 domain Ab (Sigma, LH7.2).

TABLE 8

Detection of collagen VII by collagen IV binding assay utilizing a dilution of 1:300; 1:1000; and 1:3000 of anti-collagen VII antibody (anti-NC1 domain Ab (Sigma, LH7.2) with a wash buffer of 1% BSA in PBS-0.05% Tween ® 20.

| C7 ug/mL | 1:300 dilution of anti-NC1 [OD] | | | 1:1000 dilution of anti-NC1 [OD] | | | 1:300 dilution of anti-NC1 [OD] | | |
|---|---|---|---|---|---|---|---|---|---|
| 100 | 1.0456 | 1.0882 | 0.9605 | 1.0084 | 0.9689 | 0.9681 | 0.8639 | 0.8431 | 0.8296 |
| 50 | 1.0309 | 0.9911 | 0.9464 | 0.8268 | 0.9026 | 0.83 | 0.7881 | 0.7467 | 0.6954 |
| 25 | 0.8602 | 0.7907 | 0.7892 | 0.7394 | 0.7547 | 0.702 | 0.6538 | 0.6728 | 0.5483 |
| 12.5 | 0.6233 | 0.6189 | 0.5964 | 0.5409 | 0.5205 | 0.5037 | 0.4879 | 0.4645 | 0.4182 |
| 6.3 | 0.4901 | 0.5006 | 0.487 | 0.4355 | 0.425 | 0.432 | 0.4291 | 0.4124 | 0.3389 |
| 3.1 | 0.4358 | 0.4117 | 0.4281 | 0.3876 | 0.3755 | 0.4038 | 0.3494 | 0.3147 | 0.2557 |
| 1.6 | 0.4053 | 0.4087 | 0.4104 | 0.3228 | 0.3571 | 0.3381 | 0.3432 | 0.3178 | 0.272 |
| 0 | 0.3523 | 0.363 | 0.3386 | 0.3003 | 0.2813 | 0.2981 | 0.3248 | 0.295 | 0.2295 |

Figure 3:
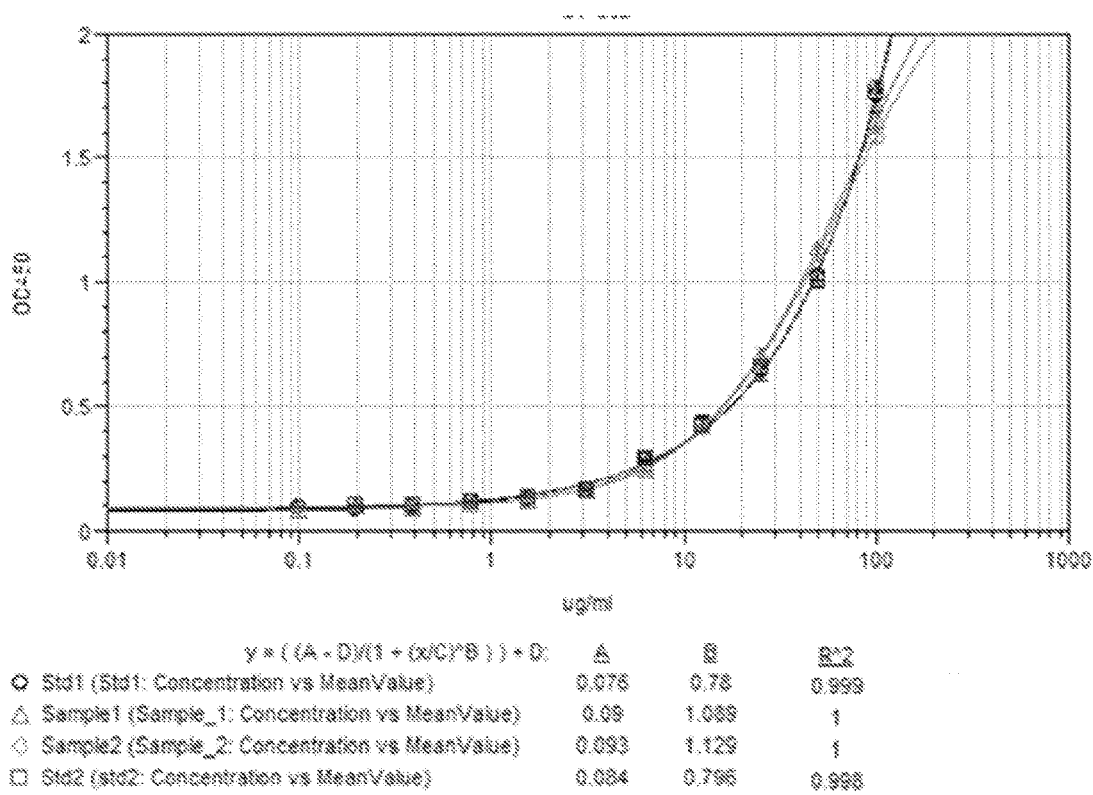
FIG. 3 show the level of collagen VII detected using the following experimental conditions: a standard/sample dilution buffer of either blocking buffer (1% BSA in 1×PBS) or culture media (serum free media for CHO cells; 8 mM L-Glu; 5% cb5 (5 dg/L); 1×HT).

Data presented in FIG. 3. was acquired using the following experimental conditions: 120 ng/well collagen IV in 20 mM $Na_2CO_3$ pH 9.2 (coating buffer); incubation of standards/samples for 2 hours at room temperature; a dilution of 1:1000; of anti-collagen VII antibody (anti-NC1 domain Ab (Sigma, LH7.2); and a wash buffer of 1% BSA in 1×PBS containing 0.05% Tween® 20. FIG. 3 shows the detection of collagen VII obtained using a standard/sample dilution buffer of either blocking buffer or culture media (serum free media for CHO cells; 8 mM L-Glu; 5% cb5 (5 dg/L); 1×HT).

Precision and repeatability of the protocol was demonstrated by diluting the Collagen VII reference standard to ten concentrations: 100, 50, 25, 12.5, 6.25, 3.1, 1.6, 0.78, 0.39, and 0.2 µg/mL in cell culture media (serum free media for CHO cells; 8 mM L-Glu; 5% cb5 (5 dg/L); 1×HT). Each standard was tested 4 times, in duplicate. The results were reported at $OD_{450}$ values. The % CV of all concentrations was ≤20% (Table 9).

TABLE 9

Precision and repeatability of collagen IV binding assay.

| C7 ug/mL | Std 1 (OD) | | | | Std 2 (OD) | | | | Std1 in culture medium (OD) | | Std2 in culture medium (OD) | | Mean (OD) | SD | % CV |
|---|---|---|---|---|---|---|---|---|---|---|---|---|---|---|---|
| 100 | 1.7034 | 1.793 | | 1.7774 | 1.7575 | 1.6142 | 1.6914 | | 1.6037 | 1.5674 | | 1.689 | 0.086 | 5.1 |
| 50 | 1.0097 | 1.0389 | | 1.0047 | 0.9891 | 1.1334 | 1.1442 | | 1.1427 | 1.0993 | | 1.070 | 0.067 | 6.2 |
| 25 | 0.6166 | 0.6774 | | 0.6723 | 0.6563 | 0.7302 | 0.6914 | | 0.7274 | 0.6525 | | 0.678 | 0.038 | 5.6 |
| 12.5 | 0.4145 | 0.4561 | | 0.4401 | 0.4064 | 0.4278 | 0.4249 | | 0.413 | 0.4189 | | 0.425 | 0.016 | 3.8 |
| 6.25 | 0.2821 | 0.292 | | 0.2807 | 0.308 | 0.2437 | 0.2632 | | 0.2592 | 0.2469 | | 0.272 | 0.023 | 8.3 |
| 3.13 | 0.1587 | 0.1661 | | 0.1704 | 0.1666 | 0.1644 | 0.164 | | 0.171 | 0.1637 | | 0.166 | 0.004 | 2.4 |
| 1.56 | 0.1305 | 0.1292 | | 0.1344 | 0.1309 | 0.1267 | 0.1281 | | 0.1395 | 0.1194 | | 0.130 | 0.006 | 4.5 |
| 0.78 | 0.124 | 0.1098 | | 0.1152 | 0.1133 | 0.1105 | 0.1073 | | 0.1118 | 0.1037 | | 0.112 | 0.006 | 5.4 |
| 0.39 | 0.0903 | 0.0983 | | 0.1007 | 0.1017 | 0.0996 | 0.0961 | | 0.1007 | 0.0972 | | 0.098 | 0.004 | 3.7 |
| 0.20 | 0.0824 | 0.0963 | | 0.1039 | 0.0982 | 0.1026 | 0.0959 | | 0.1074 | 0.0925 | | 0.097 | 0.008 | 8.0 |
| 0 | 0.0847 | 0.0897 | | 0.0979 | 0.0907 | 0.0909 | 0.0897 | | 0.0981 | 0.0855 | | 0.088 | 0.007 | 7.5 |
| 0 | 0.0836 | 0.0842 | | 0.0892 | 0.08 | 0.0751 | 0.0856 | | 0.0987 | 0.0835 | | | | |

TABLE 10

Specificity of collagen IV mediated ELISA.

| C7 ug/mL | Mean of std (OD) | Mean of Std in culture medium (OD) | Mean (OD) | % Difference |
|---|---|---|---|---|
| 100 | 1.758 | 1.619 | 1.689 | 4.11 |
| 50 | 1.011 | 1.130 | 1.070 | 5.57 |
| 25 | 0.656 | 0.700 | 0.678 | 3.30 |
| 12.5 | 0.429 | 0.421 | 0.425 | 0.96 |
| 6.25 | 0.291 | 0.253 | 0.272 | 6.88 |
| 3.13 | 0.165 | 0.166 | 0.166 | 0.10 |
| 1.56 | 0.131 | 0.128 | 0.130 | 1.09 |
| 0.78 | 0.116 | 0.108 | 0.112 | 3.24 |
| 0.39 | 0.098 | 0.098 | 0.098 | 0.33 |
| 0.20 | 0.095 | 0.100 | 0.097 | 2.26 |
| 0 | 0.088 | 0.088 | 0.088 | 0.50 |

Specificity of the protocol was demonstrated by diluting the collagen VII reference standard to ten concentrations 100, 50, 25, 12.5, 6.25, 3.1, 1.6, 0.78, 0.39, and 0.2 µg/mL in assay buffer or cell culture media (serum free media for CHO cells; 8 mM L-Glu; 5% cb5 (5 dg/L); 1×HT). Each was tested in duplicate. The results were reported at $OD_{450}$ values. The % difference between the collagen VII reference standard in assay buffer and cell culture media was ≤10% (Table 10).

The methods described in the present example showed a lower limit of detection/quantification of a mean $OD_{450}$ value for 16 zero standard replicates of 0.88 with a standard deviation of 0.0066. Adding three standard deviations to the mean $OD_{450}$ yielded a value of 0.108; to give a LLOD of 0.78 µg/mL. Adding 10 standard deviations to the mean $OD_{450}$ yielded a value of 0.154, corresponding to a LOQ of 1.13 µg/mL. The upper limit of quantification with the proposed ULOQ of the method is 100 µg/mL. The assay is expected to be linear from 0.78-100 µg/mL. This was evaluated using the standard curve by demonstrating the $R^2$ from the four parameter fit was ≥0.98.

Example 2. Exemplary Collagen IV Binding Assay for the Detection of Collagen IV Utilizing Anti-NC2 Domain Collagen VII Antibody An exemplary collagen IV binding assay for the detection and/or quantification of collagen VII is described below and in Table 13. This method utilizes an anti-NC2 domain collagen VII antibody.

A 96 well microtiter plate was coated with collagen IV at a concentration of 2 µg/mL in 20 mM $Na_2CO_3$ (pH=9.2), with 120 ng collagen IV per well (60 µl of 2 µg/mL coating solution per well); the plate was subsequently covered and incubated overnight at 2-8° C. in the dark. Following overnight incubation, the contents of the plate were dumped or aspirated. The remaining binding sites on the solid support were blocked by adding 200 µl of blocking buffer (1% BSA in 1×PBS); the plate was subsequently covered and incubated for 1 hour at 25° C. (room temperature). Post blocking the contents of the plate were dumped or aspirated and the plate was washed three times with 300 µl of wash buffer (1.0% BSA in 1×PBS+0.05% Tween® 20).

The reference standard collagen VII was diluted in collagen dilution buffer (1% BSA in 1×PBS) to a concentration of 100 µg/mL, and subsequently diluted to obtain the following standard curve (Table 11).

TABLE 11

Standard Curve Reference Standard Collagen VII

| Final Concentration (µg/mL) | µL | Of (µg/mL) | + | µL of Dilution Buffer |
|---|---|---|---|---|
| 100 | 600 | 100 | + | 0 |
| 50 | 300 | 100 | + | 300 |
| 25 | 300 | 50 | + | 300 |
| 12.5 | 300 | 25 | + | 300 |
| 6.25 | 300 | 12.5 | + | 300 |
| 3.13 | 300 | 6.25 | + | 300 |
| 1.56 | 300 | 3.13 | + | 300 |
| 0.78 | 300 | 1.56 | + | 300 |

Samples containing collagen VII for analysis can be prepared and diluted in dilution buffer, if necessary. One hundred µl of each of the standards and samples was added to designated coated and blocked wells of the microtiter plate, the plate subsequently sealed and incubated at 25° C. (room temperature) for 2 hours. Post standard/sample incubation the contents of the plate were dumped or aspirated and the plate was washed four times with 300 µl of wash buffer (1.0% BSA in 1×PBS+0.05% Tween® 20), blotting the plate on a paper towel between each wash step to remove excess liquid.

One hundred µl of rabbit anti-human collagen VII anti-NC2 polyclonal antibody (primary antibody) was diluted 1:300 in dilution buffer (1% BSA in 1×PBS), added to each well; and the plate subsequently sealed and incubated at 25° C. (room temperature) for one hour. Post primary antibody incubation the contents of the plate were dumped or aspirated and the plate was washed four times with 300 µl of wash buffer (1.0% BSA in 1×PBS+0.05% Tween® 20), blotting the plate on a paper towel between each wash step to remove excess liquid.

One hundred µl of Goat Anti-rabbit IgG HRP (detecting antibody) was diluted 1:5000 in a dilution buffer (1% BSA in 1×PBS), added to each well; and the plate subsequently sealed and incubated at 25° C. (room temperature) for one hour. Post detecting antibody incubation the contents of the plate were dumped or aspirated and the plate was washed five times with 300 µl of wash buffer (1.0% BSA in 1×PBS+0.05% Tween® 20), blotting the plate on a paper towel between each wash step to remove excess liquid.

The HRP mediated reaction was carried out by adding 100 µl of the HRP substrate TMB (substrate) to each well, and subsequently sealing and incubating the plate for 20 minutes at 25° C. in the dark. The reaction was stopped by adding 50 µl of 1M sulfuric acid (stop solution); adding the stop solution in the same order the TMB was added. The microtiter plate was then read by an absorbance plate reader at $A_{450}$ nm within 30 minutes of adding the stop solution to quantitate the amount of collagen VII in each standard/sample. The data was analyzed using a 4-parameter fit of the standard curve data; using Softmax Pro software to calculate the concentration of the samples from the standard curve using the 4-paramter fit. Softmax Pro software was also used to calculate the standard curve parameters (e.g., $R^2$), mean values, and % coefficients of variation (% CV) for the control and test samples.

The test was considered valid if the following standard curve and control criteria were met: 1) The % CV's of 1.56-100 µg/mL standards were ≤20%. This requirement did not apply to the 0.78 µg/mL standard. 2) $R^2$-value for the standard curve was ≥0.980.

The result for a test sample was considered valid if the following criteria were met: 1) The $OD_{450}$ of three sample replicates was within the range of the standard curve (0.78 µg/mL to 100) and the % CV of the values was ≤20%.

Figure 4:
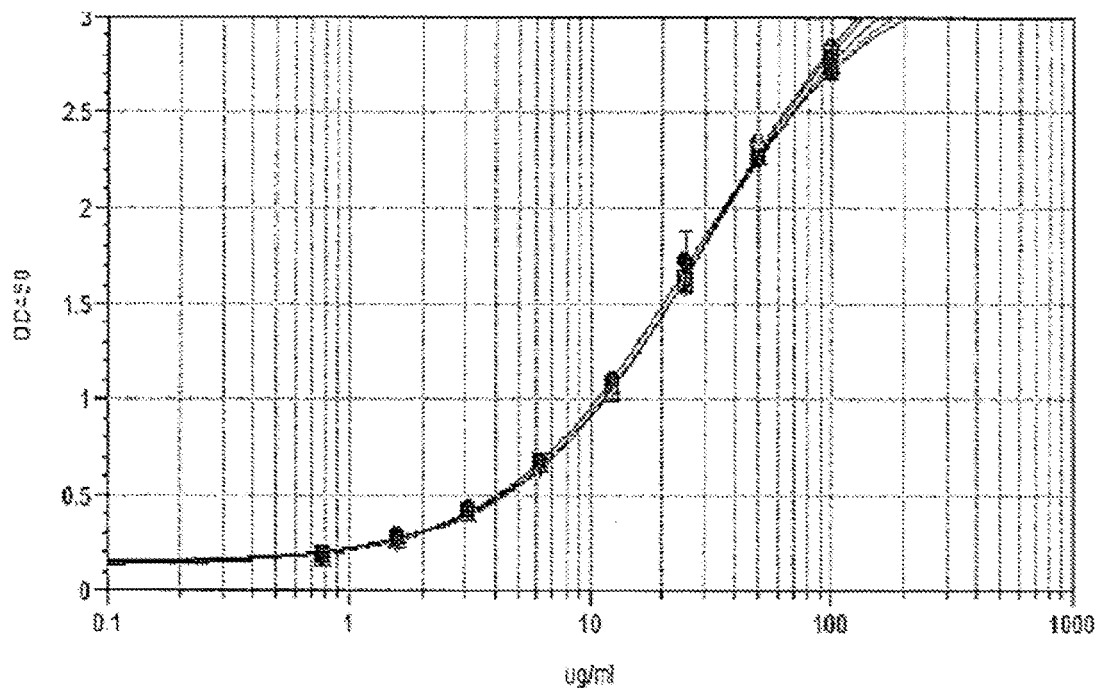
FIG. 4 show the level of collagen VII detected using an anti-NC2 domain collagen VII antibody for detection of collagen VII.

The exemplary results are described in Table 12 and FIG. 4. Table 12 displays the OD values for 5 standards, each in duplicate, along with the mean and % CV for each standard concentration.

TABLE 12

Collagen VII detection by collagen IV binding assay utilizing anti-NC2 domain collagen VII antibody.

| Standard (µg/mL) | Standard 1 | | Standard 2 | | Standard 3 | | Standard 4 | | Standard 5 | | Mean | % CV |
|---|---|---|---|---|---|---|---|---|---|---|---|---|
| 100 | 2.8365 | 2.8295 | 2.8242 | 2.7914 | 2.7891 | 2.7218 | 2.6950 | 2.7261 | 2.6953 | 2.7588 | 2.7667 | 2.0 |
| 50 | 2.3541 | 2.3171 | 2.3076 | 2.3093 | 2.2933 | 2.2638 | 2.3480 | 2.2618 | 2.2358 | 2.2746 | 2.2965 | 1.7 |
| 25 | 1.6123 | 1.6287 | 1.6387 | 1.6281 | 1.6640 | 1.6219 | 1.5723 | 1.6278 | 1.6187 | 1.8372 | 1.6449 | 4.3 |
| 12.5 | 1.0608 | 1.0667 | 1.0146 | 1.1012 | 1.0334 | 1.0626 | 1.0322 | 1.0579 | 1.0782 | 1.1151 | 1.0622 | 2.9 |
| 6.25 | 0.6527 | 0.6373 | 0.6753 | 0.6826 | 0.6710 | 0.6815 | 0.6384 | 0.6572 | 0.9854 | 0.6593 | 0.6640 | 2.7 |
| 3.13 | 0.4030 | 0.4050 | 0.4096 | 0.4122 | 0.3958 | 0.4267 | 0.4207 | 0.4283 | 0.4144 | 0.4427 | 0.4158 | 3.4 |
| 1.56 | 0.2724 | 0.2592 | 0.2555 | 0.2683 | 0.2750 | 0.2637 | 0.2336 | 0.2695 | 0.2790 | 0.2772 | 0.2653 | 5.1 |
| 0.78 | 0.1772 | 0.1748 | 0.1773 | 0.1931 | 0.1759 | 0.1835 | 0.1803 | 0.1797 | 0.1885 | 0.2013 | 0.1831 | 4.7 |
| 0 | 0.1282 | 0.1425 | 0.1234 | 0.1165 | 0.1313 | 0.1304 | 0.1129 | 0.1189 | 0.1053 | 0.1148 | 0.1234 | 8.4 |

TABLE 13

Exemplary conditions for collagen IV binding assay utilizing anti-NC2 domain
Collagen VII antibody for quantification of collagen VII.

| ELISA Step | Reagent/Concentration | Volume | Conditions |
|---|---|---|---|
| Coat plate | 2 ug/mL Collagen IV in 20 mM $Na_2CO_3$, pH 9.2 buffer, 120 ng/well | 60 μl | Overnight at 2-8° C. |
| Block | 1% BSA in 1XPBS (Blocking Buffer) | 200 μl | 1 hr at 25° C. |
| Wash | 1.0% BSA in 1XPBS + 0.05% Tween® 20 (Wash Buffer) | 300 μl | 3X |
| Standards/Samples | 100 to 0.78 ug/mL collagen VII standard (two-fold serial, 8 points dilution, in triplicate) in Block buffer (1% BSA in 1XPBS) | 100 μl | 2 hr at 25° C. |
| Wash | 1.0% BSA in 1XPBS + 0.05% Tween® 20 | 300 μl | 4X |
| anti-Collagen VII Antibody | Rabbit anti-human Collagen VII anti-NC2 polyclonal antibody (1:300 dilution in Blocking buffer) | 100 μl | 1 hr at 25° C. |
| Wash | 1.0% BSA in 1XPBS + 0.05% Tween® 20 | 300 μl | 4X |
| Detection antibody | Goat Anti-rabbit IgG-RP (1:5000 dilution in Blocking Buffer) | 100 μl | 1 hr at 25° C. |
| Wash | 1.0% BSA in 1XPBS + 0.05% Tween® 20 | 300 μl | 5X |
| Substrate | TMB | 100 μl | 20 min at 25° C. |
| Stop | 1M Sulfuric Acid | 50 μl | N/A |
| Plate read | A450 | N/A | Read plate within 30 min of adding stop solution |

Example 3. Exemplary Collagen IV Mediated Collagen VII ELISA for the Detection of Collagen IV Utilizing Anti-NC1 Domain Collagen VII Antibody An exemplary collagen IV binding assay for the detection and/or quantification of collagen VII is described below and in Table 14. This protocol utilizes an anti-NC1 domain collagen VII antibody.

Briefly, a 96 well microtiter plate was coated with collagen IV at a concentration of 2 μg/mL in 20 mM $Na_2CO_3$ (pH=9.2) (coating buffer), with 120 ng collagen IV per well; and the plate subsequently covered and incubated overnight at 4° C. Following overnight incubation, the contents of the plate were dumped or aspirated. The remaining binding sites on the solid support were blocked by adding 200 μl of blocking buffer (1% BSA in 1xPBS); the plate was subsequently covered and incubated for 1 hour at 25° C. (room temperature). Post blocking the contents of the plate were dumped or aspirated and the plate was washed four times with 300 μl with 300 μl of 1.0% BSA in 1xPBS.

The collagen VII reference standards were prepared and samples for analysis diluted, if necessary, both in dilution buffer (1% BSA in 1xPBS). One hundred μl of each of the collagen VII reference standards and samples were added to designated coated and blocked wells of the microtiter plate; the plate subsequently sealed and incubated at 25° C. (room temperature) for 2 hours. Post standard/sample incubation the contents of the plate were dumped or aspirated and the plate was washed five times with 300 μl of wash buffer (1.0% BSA in 1xPBS+0.05% Tween® 20), blotting the plate on a paper towel between each wash step to remove excess liquid.

One hundred μl of mouse anti-collagen VII NC1-domain antibody (primary antibody) was diluted 1:1000 in dilution buffer (1% BSA in 1xPBS), added to each well; and the plate subsequently sealed and incubated at 25° C. (room temperature) for one hour. Post primary antibody incubation the contents of the plate were dumped or aspirated and the plate was washed five times with 300 μl of wash buffer (1.0% BSA in 1xPBS+0.05% Tween® 20), blotting the plate on a paper towel between each wash step to remove excess liquid.

One hundred μl of goat anti-mouse IgG-HRP (detecting antibody) was diluted 1:5000 in a dilution buffer (1% BSA in 1xPBS), added to each well; and the plate subsequently sealed and incubated at 25° C. (room temperature) for one hour. Post detecting antibody incubation the contents of the plate were dumped or aspirated and the plate was washed six times with 300 μl of wash buffer (1.0% BSA in 1xPBS+ 0.05% Tween® 20), blotting the plate on a paper towel between each wash step to remove excess liquid.

The HRP mediated reaction is carried out by adding 100 μl of the HRP substrate TMB (substrate) to each well, and subsequently sealing and incubating the plate for 20 minutes at 25° C. in the dark. The reaction was stopped by adding 50 μl of 1M sulfuric acid (stop solution), adding the stop solution in the same order the TMB was added. The microtiter plate was then read by an absorbance plate reader at A450 nm within 30 minutes of adding the stop solution to quantitate the amount of collagen VII in each sample. The data was analyzed using a 4-paramter fit of the standard curve data; using the software to calculate the concentration of the samples from the standard curve using the 4-paramter fit. Softmax Pro software was also used to calculate the standard curve parameters (e.g., $R^2$), mean values, and % coefficients of variation (% CV) for the control and test samples.

TABLE 14

Exemplary conditions for collagen IV binding assay utilizing anti-NC1 domain Collagen VII antibody for quantification of collagen VII.

| ELISA Step | Reagent/Concentration | Volume | Conditions |
| --- | --- | --- | --- |
| Coat plate | 2 ug/mL Collagen IV in 20 mM $Na_2CO_3$, pH 9.2 buffer, 120 ng/well | 60 μl | Overnight at 4° C. |
| Block | 1% BSA in 1XPBS | 200 μl | 1 hr at RT |
| Wash | 1.0% BSA in 1XPBS | 300 μl | 4X |
| Standards/Samples | 100 to 0.78 ug/mL collagen VII standard (two-fold serial, 8 points dilution) in Block buffer | 100 μl | 2 hr at RT |
| Wash | 1.0% BSA in PBST (0.05% Tween ® 20 in PBS) | 300 μl | 5X |
| anti-Collagen VII Antibody | Anti-mouse Collagen VII antibody (LH 7.2) (sigma: C-6805), 1:1000 dilution in Block buffer | 100 μl | 1 hr at RT |
| Wash | 1.0% BSA in PBST | 300 μl | 5X |
| Detection antibody | Goat Anti-mouse IgG_HRP (1:5000 diluted in Blocking Buffer) | 100 μl | 1 hr at RT |
| Wash | 1.0% BSA in PBST | 300 μl | 6X |
| Substrate | TMB | 100 μl | 30 min at 25° C. |
| Stop | 1M Sulfuric Acid | 50 μl | N/A |
| Plate read | A450 | N/A | N/A |

Example 4. Comparison of Laminin 332 Mediated Collagen VII ELISA and Collagen IV Mediated Collagen VII ELISA for Detection of Collagen VII Laminin 332 has been used as a substrate in ELISAs to detect collagen VII. Collagen IV mediated collagen VII ELISAs were compared to those utilizing laminin 332 as a substrate to quantify collagen VII. An exemplary laminin 332 mediated collagen VII ELISA conducted using 0.6 μg/well laminin 332; subsequently incubating with 40 μg/well collagen VII; and utilizing 1:300 dilution of anti-collagen VII antibody, specifically an anti-NC1 domain antibody (Sigma LH7.2) for detection. As shown in Table 15, use of laminin 332 ELISA is able to detect collagen VII.

TABLE 15

Collagen VII detection by laminin 332 mediated ELISA utilizing anti-NC1 domain collagen VII antibody.

| Collagen VII [μg/mL] | mAb anti-NC1 domain Collagen VII (Sigma LH7.2) [O.D.] | |
| --- | --- | --- |
| 40 | 0.842 | 0.669 |
| 0 | 0.237 | 0.23 |

An exemplary collagen IV mediated ELISA was conducted utilizing 0.3 μg/well collagen IV in 20 mM $Na_2CO_3$, pH 9.2; incubating with 40 μg/well collagen VII; and utilizing 1:300 dilution of the anti-NC1 domain anti-collagen VII antibody (Sigma LH7.2) for detection. As shown in Table 16 use of collagen IV mediated ELISA is able to detect collagen VII. As the results show, the use of collagen IV as a substrate is able to detect higher levels of collagen VII than the use of laminin 332.

TABLE 16

Collagen VII detection by collagen IV binding assay utilizing anti-NC1 domain collagen VII antibody.

| Collagen VII [μg/mL] | mAb anti-NC1 domain Collagen VII (Sigma LH7.2) [O.D.] | |
| --- | --- | --- |
| 40 | 1.941 | 1.922 |
| 0 | 0.5502 | 0.4787 |

What is claimed is:

1. A method of detecting and/or quantifying collagen VII or a fragment thereof in a sample, the method comprising:
    contacting the sample with collagen IV or a fragment thereof which binds to collagen VII; and
    contacting the sample with an anti-collagen VII antibody, wherein the anti-collagen VII antibody consists of an antibody that binds to the NC2 domain of collagen VII;
    detecting binding of the anti-collagen VII antibody to thereby detect and/or quantify an amount of collagen VII or the fragment thereof in the sample.

2. The method of claim 1, wherein full length collagen VII is detected or quantified.

3. The method of claim 1, wherein collagen VII or a fragment thereof comprising both the NC1 and NC2 domains is detected or quantified.

4. The method of claim 1, further comprising subsequently contacting the sample with a second anti-collagen VII antibody, which binds to an epitope of collagen VII or a fragment thereof which is accessible after the binding of collagen VII or a fragment thereof to collagen IV or the fragment thereof, wherein the second anti-collagen VII antibody binds to the NC1 domain of collagen VII.

5. The method of claim 1, further comprising contacting the sample with a second antibody, which binds to the anti-collagen VII antibody.

6. The method of claim 5, comprising detecting the presence of the anti-collagen VII antibody.

7. The method of claim 5, comprising quantifying the amount of anti-collagen VII antibody.

8. The method of claim 1, further comprising measuring the level of collagen VII bound to collagen IV.

9. The method of claim 1 wherein, the collagen IV or the fragment thereof is disposed on a support.

10. The method of claim 1 wherein, the sample is a biological sample.

11. The method of claim 1 wherein, the sample is a drug product preparation or a drug substance preparation.

12. The method of claim 1,
wherein the anti-collagen VII antibody binds to an epitope of the NC2 domain of collagen VII, which is accessible after the binding of collagen VII or a fragment thereof to collagen IV or the fragment thereof.

13. A method of evaluating or processing a collagen VII sample, wherein the method comprises
acquiring an evaluation of the presence or amount of collagen VII;
providing a determination of whether the value determined meets a preselected criteria;
thereby evaluating or processing the collagen VII preparation, wherein the presence or amount of collagen VII is determined by a method comprising:
contacting the sample with collagen IV or a fragment thereof which binds to collagen VII;
contacting the sample with an anti-collagen VII antibody, wherein the anti-collagen VII antibody consists of an antibody that binds to the NC2 domain of collagen VII; and
detecting binding of collagen VII or a fragment thereof to collagen IV or the fragment thereof, to thereby detect and/or quantify the amount of collagen VII or the fragment thereof in the sample.

14. The method of claim 13, wherein the method further comprises providing a comparison of the value determined with a reference value to thereby evaluate the sample.

15. The method of claim 13, wherein the sample is further processed depending on whether a preselected relationship is met.

16. The method of claim 13, wherein the anti-collagen VII antibody binds to an epitope of the NC2 domain of collagen VII or a fragment thereof which is accessible after the binding of collagen VII or a fragment thereof to collagen IV or the fragment thereof.

17. The method of claim 16, further comprising contacting the sample with a second anti-collagen VII antibody, which binds to an epitope of collagen VII or a fragment thereof which is accessible after the binding of collagen VII or a fragment thereof to collagen IV or the fragment thereof, wherein the second anti-collagen VII antibody binds to the NC1 domain of collagen VII.

* * * * *